(12) United States Patent
Eshoo et al.

(10) Patent No.: US 10,011,866 B2
(45) Date of Patent: Jul. 3, 2018

(54) NUCLEIC ACID LIGATION SYSTEMS AND METHODS

(71) Applicant: IBIS BIOSCIENCES, INC., Carlsbad, CA (US)

(72) Inventors: Mark W. Eshoo, San Diego, CA (US); John Picuri, Carlsbad, CA (US); Stanley T. Motley, Carlsbad, CA (US); Curtis Phillipson, Carlsbad, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 0 days.

(21) Appl. No.: 15/362,410

(22) Filed: Nov. 28, 2016

(65) Prior Publication Data
US 2017/0145493 A1    May 25, 2017

Related U.S. Application Data

(62) Division of application No. 14/369,641, filed as application No. PCT/US2012/072089 on Dec. 28, 2012, now Pat. No. 9,506,113.

(60) Provisional application No. 61/580,925, filed on Dec. 28, 2011.

(51) Int. Cl.
| | |
|---|---|
| *C12P 19/34* | (2006.01) |
| *C12Q 1/6855* | (2018.01) |
| *C12N 15/11* | (2006.01) |
| *C07H 21/04* | (2006.01) |

(52) U.S. Cl.
CPC ............ *C12Q 1/6855* (2013.01); *C12N 15/11* (2013.01)

(58) Field of Classification Search
None
See application file for complete search history.

(56) References Cited

U.S. PATENT DOCUMENTS 9,506,113 B2 * 11/2016 Eshoo ..................... C12P 19/34
2004/0209299 A1 * 10/2004 Pinter ................ C12N 15/1093
435/6.12

* cited by examiner

*Primary Examiner* — Nancy J Leith
(74) *Attorney, Agent, or Firm* — Casimir Jones, S.C.; David Casimir

(57) ABSTRACT

The present disclosure relates to systems and methods for nucleic acid ligation. In particular, the present disclosure provides oligonucleotide adaptors for use in nucleic acid ligation reactions.

15 Claims, 2 Drawing Sheets

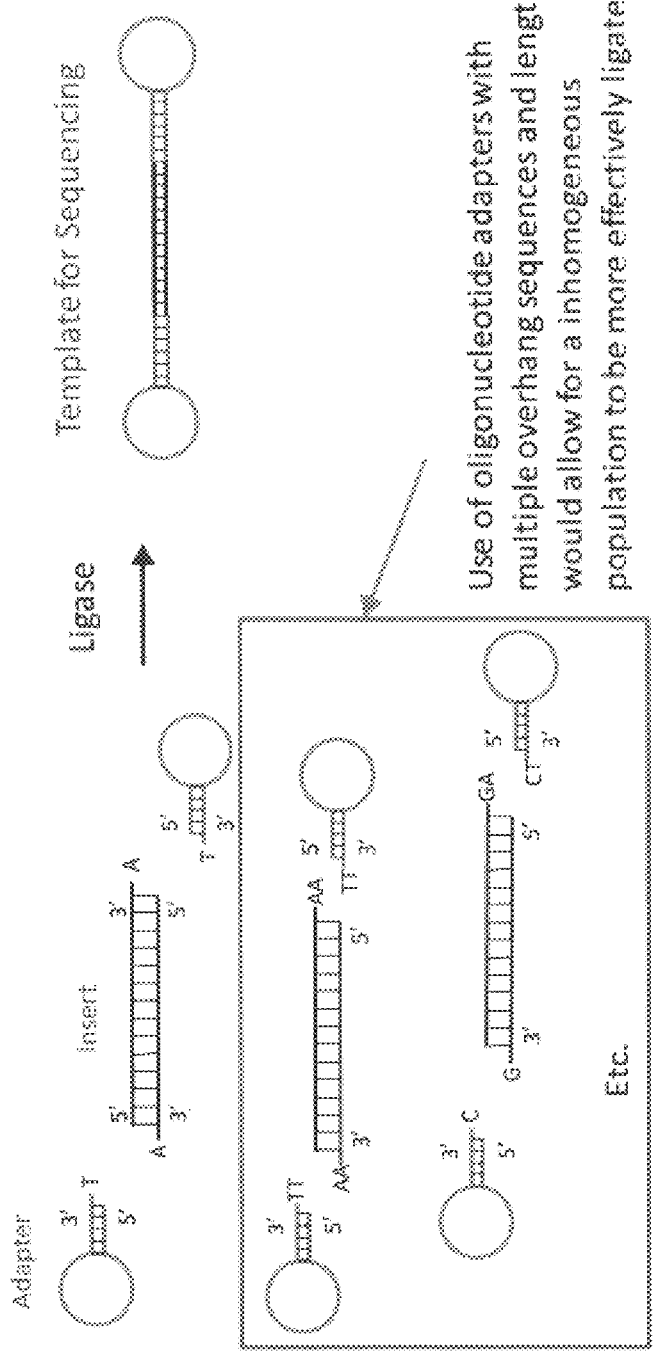

NUCLEIC ACID LIGATION SYSTEMS AND METHODS

CROSS-REFERENCE TO RELATED APPLICATIONS

The present Application claims priority to U.S. Provisional Application Ser. No. 61/580,925 filed Dec. 28, 2011, the entirety of which is incorporated by reference herein.

STATEMENT REGARDING FEDERALLY SPONSORED RESEARCH OR DEVELOPMENT

This invention was made with government support under HDTRA1-10-C-0080 awarded by the Defense Threat Reduction Agency. The government has certain rights in the invention.

FIELD OF INVENTION

The present disclosure relates to systems and methods for nucleic acid ligation. In particular, the present disclosure provides oligonucleotide adaptors for use in nucleic acid ligation reactions.

BACKGROUND

Sequencing of nucleic acids continues to be one of the most important and useful ways to analyze DNA and RNA samples. Recent developments have made possible highly parallel high throughput sequencing. Many of these approaches use an in vitro cloning step to generate many copies of each individual molecule. Emulsion PCR is one method, isolating individual DNA molecules along with primer-coated beads in aqueous bubbles within an oil phase. A polymerase chain reaction (PCR) then coats each bead with conal copies of the isolated library molecule and these beads are subsequently immobilized for later sequencing (See, e.g. WO04069849A2 and WO05010145A2). In other cases, surface methods of conal amplification have been developed, for example, by the use of bridge PCR where fragments are amplified upon primers attached to a solid surface. These methods produce many physically isolated locations which each contain many copies of a single fragment. While these methods have provided improvements in sequencing throughput, there is a continuing need to improve the methods of obtaining samples appropriate for sequencing, and of handling, storing, and amplifying such samples. In particular, there is a need to improve methods for obtaining high throughput sequencing data for a specific set of genes or gene products from whole genome or transcriptome samples.

Therefore, there is a need for improved methods of cloning, obtaining, storing, amplifying, and analyzing nucleic acid samples.

SUMMARY

The present disclosure relates to systems and methods for nucleic acid ligation. In particular, the present disclosure provides oligonucleotide adaptors for use in nucleic acid ligation reactions.

Embodiments of the present invention provide kits, systems and methods for ligating nucleic acids to adaptors. For example, in some embodiments, the present invention provides a ligation method and kit for performing a ligation reaction, comprising: a) contacting a nucleic acid insert comprising nucleotide overhangs (e.g., a double stranded nucleic acid with single stranded overhangs) with a plurality of nucleic acid adaptors, wherein the adaptors each have a distinct single stranded overhang relative to the others (e.g., a double stranded nucleic acid with single stranded overhangs); and b) ligating the adaptors to the inserts with a ligase enzyme to generate ligated inserts. In some embodiments, the adaptors comprise overhangs of 1 and/or 2 nucleotides. In some embodiments, the overhangs have random nucleotide sequences or a plurality of distinct sequences designed to hybridize to nucleotide overhangs of the inserts. In some embodiments, the inserts comprise a plurality of inserts (e.g., a population or library) with distinct nucleic acid sequences. In some embodiments, each of the single stranded nucleotide overhangs of the inserts have a plurality of distinct sequences. In some embodiments, the single stranded nucleotide overhangs of the inserts comprise overhangs of 1 and/or 2 nucleotides. In some embodiments, the adaptors have single nucleotide overhangs at the 3' and/or 5' ends (e.g., the same or different and are selected from a, t, c, or g). In some embodiments, the adaptors have double nucleotide overhangs at the 3' and/or 5' ends (e.g., the same or different and are selected from aa, ag, at, ac, ga, gg, gc, gt, tt, tc, ta, tg, cc, ct, ca, or cg). In some embodiments, the adaptors comprise 2 or more, 3 or more, 4 or more, 5 or more, 6 or more, 7 or more, 8 or more, 9 or more, 10 or more, 11 or more, 12 or more, 13 or more, 14 or more, 15 or more or all 16 distinct overhangs. In some embodiments, the methods further comprise the step of analyzing said ligated inserts (e.g., via sequencing).

Further embodiments of the present invention provide compositions, systems and kits for ligating nucleic acids to adaptors (e.g., comprising a plurality of nucleic acid adaptors, wherein the adaptors each have a distinct single stranded overhang relative to the others (e.g., a double stranded nucleic acid with single stranded overhangs)) and additional components necessary, sufficient or useful for performing ligation reactions.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 2 shows an overview of a ligation reaction with multiple adaptor overhangs.

DETAILED DESCRIPTION

Figure 1:
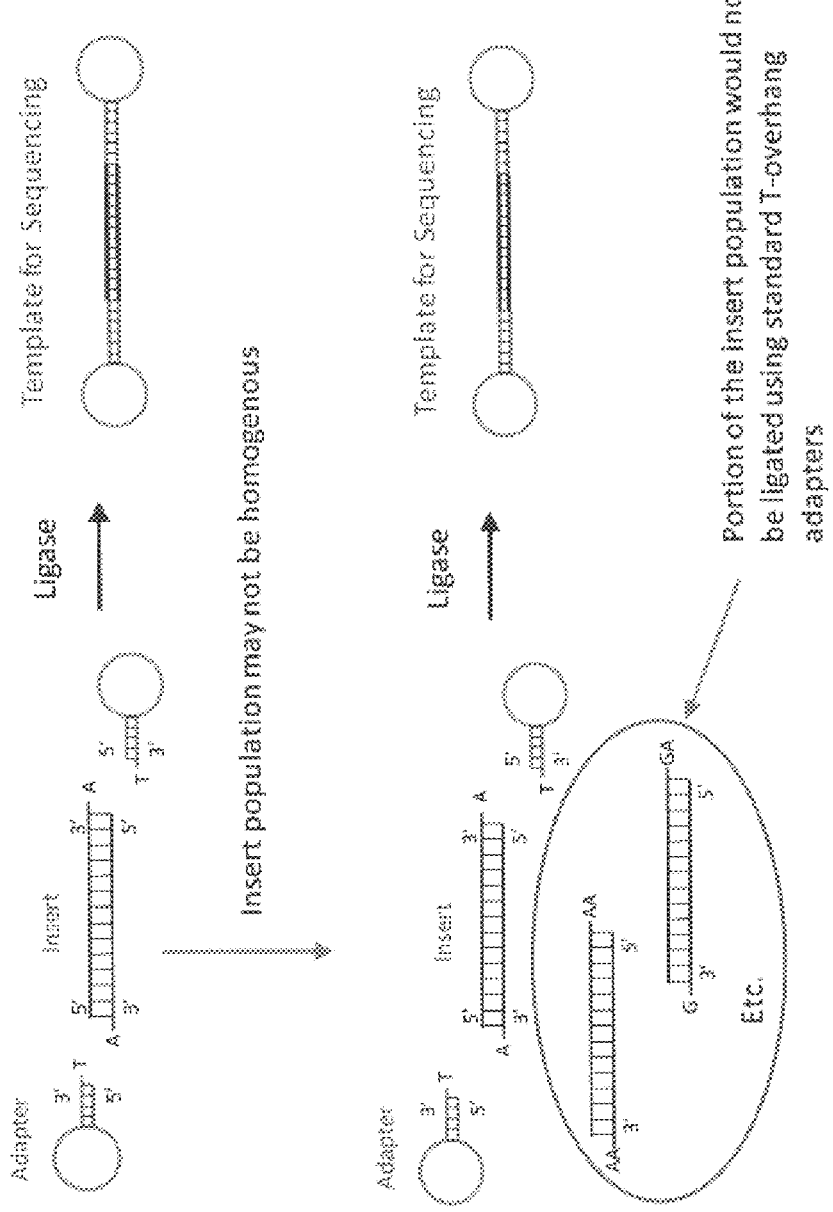
FIG. 1 shows an overview of a T-A ligation scheme.

The present disclosure relates to systems and methods for nucleic acid ligation. In particular, the present disclosure provides oligonucleotide adaptors for use in nucleic acid ligation reactions.

Definitions

To facilitate an understanding of the present technology, a number of terms and phrases are defined below. Additional definitions are set forth throughout the detailed description.

As used herein, "a" or "an" or "the" can mean one or more than one. For example, "a" widget can mean one widget or a plurality of widgets.

As used herein, the term "insert" refers to a nucleic acid sequence of interest. In some embodiments, inserts are double stranded DNAs that comprise single stranded nucleotide overhangs at the 5' and/or 3' ends. Is some embodiments, the single stranded overhangs are 1, 2 or more nucleotides. In some embodiments, inserts are generated via amplification by a nucleic acid polymerase or by a restriction enzyme. In some embodiments, inserts are provided as a library or population of inserts with a plurality of distinct sequences, both in the double stranded regions and the single stranded overhangs.

As used herein, the term "adaptor" refers to a double stranded DNA (e.g., oligonucleotides) that comprises single stranded nucleotide overhangs at the 5' and/or 3' ends. Is some embodiments, the single stranded overhangs are 1, 2 or more nucleotides. In some embodiments, adaptors comprise additional nucleic acid sequence for cloning or analysis of "inserts." In some embodiments, adaptors comprise labels or affinity tags for analysis or purification of "inserts."

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer should be sufficiently long to prime the synthesis of extension products in the presence of the inducing agent. The exact lengths of the primers will depend on many factors, including temperature, source of primer and the use of the method.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

"Solid support" as used herein refers to any solid surface to which nucleic acids can be attached, such as for example, including but not limited to, metal surfaces, latex beads, dextran beads, polystyrene surfaces, polypropylene surfaces, polyacrylamide gel, gold surfaces, glass surfaces and silicon wafers.

As used herein, the terms "subject" and "patient" refer to any animal, such as a dog, a cat, a bird, livestock, and particularly a mammal, and preferably a human.

As used herein, the term "sample" is used in its broadest sense. In one sense, it is meant to include a representative portion or culture obtained from any source, including biological and environmental sources. Biological samples may be obtained from animals (including humans) and encompass fluids, solids, tissues, and gases. Biological samples include blood products, such as plasma, serum, and the like. Environmental samples include environmental material such as surface matter, soil, mud, sludge, biofilms, water, and industrial samples. Such examples are not however to be construed as limiting the sample types applicable to the present invention.

Embodiments of the Technology

Although the disclosure herein refers to certain illustrated embodiments, it is to be understood that these embodiments are presented by way of example and not by way of limitation.

Ligation reactions are used quite frequently in biochemical reaction schemes (e.g., next generation sequencing) and there are many methods depending on the specific application. Many ligation methods utilize either a blunt or TA mediated ligation, usually using a variant of T4 DNA ligase.

During library preparation (e.g., for sequencing or other nucleic acid analysis technique), an oligonucleotide adapter is ligated onto the sample DNA in order to perform the sequencing reaction. Before the ligation process the sample DNA often has an untemplated A added to the 3' ends of the sample DNA to limit concatamers and increase specificity during the ligation reaction. The addition of an untemplated A, however, is not always limited to one base in length nor is it only A's which are added potentially leading to a sample population with multiple different overhang sequences. End polishing and A tailing of DNA fragments can lead to a variety of different nucleotides at the 5' overhang besides the desired A overhang.

In a typical ligation scheme only adapters with T overhangs (which are complementary to the expected A overhang on the sample DNA) are added during ligation. These adapters readily ligate to sample DNA with the expected A overhangs but will not ligate to molecules with any other overhang (different sequences and/or different overhang lengths), thus reducing the efficiency of the ligation reaction and downstream analysis.

Accordingly, in some embodiments, the present disclosure overcomes this limitation by providing adaptors with a mixture of overhang sequences. Using adapters with a mixture of overhang sequences and/or lengths, allows for the entire population of the sample DNA to be ligated and subsequently sequenced. Additionally, as some of the overhang combinations have the potential to ligate more quickly than the T-A combination, the use of multiple adaptors with different sequences provides an acceleration of the ligation reaction. The use of multiple different overhangs allows for efficient ligation of products with overhangs of varied or unknown sequences.

In some embodiments, the present invention provides kits, systems and methods for performing ligation reactions. In some embodiments, ligation reactions are made up of a ligase or combination of ligases (e.g. T4 DNA ligase, E. coli ligase, etc.), oligonucleotide adapters with multiple different overhangs (e.g., a specific known set or a degenerate set depending on application) and a sample to ligate the adapters to (e.g., such as a next generation sequencing library).

FIG. 2 illustrates an exemplary embodiment of the technology described herein. An insert (e.g., sequence of interest) with multiple overhanging nucleotides is contacted with oligonucleotide adaptors comprising a plurality of different single or double nucleotide overhangs. In some embodiments, the overhangs have random degenerate overhangs. In other embodiments, the overhangs are targeted to the population of inserts.

In some embodiments, adaptors comprise single nucleotide overhangs at the 3' and/or 5' ends. In other embodiments, adaptors comprise 2 nucleotide overhangs at the 3' and/or 5' ends. In still further embodiments, adaptors comprise overhangs of 3 or more nucleotides at the 3' and/or 5' ends. In some embodiments, the 3' and 5' ends comprise overhangs of the same or different lengths (e.g., 1 nucleotide at the 3' end and 1 nucleotide at the 5' end, 1 nucleotide at the 3' end and 2 nucleotides at the 5' end, 2 nucleotides at the 3' end and 1 nucleotide at the 5' end, or 2 nucleotides at the 3' end and 2 nucleotides at the 5' end. In some embodiments, the 3' and 5' overhangs comprise the same or different nucleotide overhangs. Overhangs may be any nucleotide. For example, single base overhangs may be any combination of one or more of c, t, a or g. Double nucleotide overhangs may be any combination of aa, ag, at, ac, ga, gg, gc, gt, tt, tc, ta, tg, cc, ct, ca, cg. In some embodiments, a population of adaptors comprise 2 or more, 3 or more, 4 or more, 5 or more, 6 or more, 7 or more, 8 or more, 9 or more, 10 or more, 11 or more, 12 or more, 13 or more, 14 or more, 15 or more or all 16 distinct overhangs. In some embodiments, populations comprise one or more adaptors with 3 nucleotide overhangs.

The adaptors (e.g., comprising tags, cloning sequences, affinity labels, detection labels, etc.) are hybridized to the insert using one or more suitable ligases. The cloned inserts are then available for use in a variety of applications.

The compositions and methods described herein find use in a variety of nucleic acid analysis methods in research, screening, clinical, therapeutic applications. The compositions and methods find use in any ligation reactions where there is the potential for a mixture of sample overhangs in both sequence and length. Examples of applications include, but are not limited to, cloning for research and industrial uses, preparation of libraries for microarray analysis, differential display analysis (See e.g., Liang et al., Cancer Res. 1992 Dec. 15; 52(24):6966-8; herein incorporated by reference in its entirety), and preparation of libraries for sequencing. Exemplary methods are described below Embodiments of the present invention are illustrated for use in next generation sequencing library preparation (e.g., single tube and microfluidic formats where purification between steps is limited or non-existent). However, the present invention is not limited to next generation sequencing and finds use in variety of applications.

A. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

A variety of nucleic acid sequencing methods are contemplated for use in the methods of the present disclosure including, for example, chain terminator (Sanger) sequencing, dye terminator sequencing, and high-throughput sequencing methods. Many of these sequencing methods are well known in the art. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in *Genomics,* 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. No. 6,432,360, U.S. Pat. No. 6,485,944, U.S. Pat. No. 6,511,803; herein incorporated by reference in their entireties), the 454 picotiter pyrosequencing technology (Margulies et al., 2005 Nature 437, 376-380; US 20050130173; herein incorporated by reference in their entireties), the SOLEXA® single base addition technology (Bennett et al., 2005, Pharmacogenomics, 6, 373-382; U.S. Pat. No. 6,787,308; U.S. Pat. No. 6,833,246; herein incorporated by reference in their entireties), the LYNX massively parallel signature sequencing technology (Brenner et al. (2000). Nat. Biotechnol. 18:630-634; U.S. Pat. No. 5,695,934; U.S. Pat. No. 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbiol., 7: 287-296; each herein incorporated by reference in their entirety). NGS methods can be broadly divided into those that typically use template amplification and those that do not. Amplification-requiring methods include pyrosequencing commercialized by Roche as the 454® technology platforms (e.g., GS™ 20 and GS FLX™), the SOLEXA® platform commercialized by ILLUMINA®, and the Supported Oligonucleotide Ligation and Detection (SOLID™) platform commercialized by Applied Biosystems. Non-amplification approaches, also known as single-molecule sequencing, are exemplified by the HELISCOPE® platform commercialized by Helicos BioSciences, and emerging platforms commercialized by VisiGen, Oxford Nanopore Technologies Ltd., Life Technologies/ION TORRENT™, and Pacific Biosciences, respectively.

In pyrosequencing (Voelkerding et al., Clinical Chem., 55: 641-658, 2009; MacLean et al., Nature Rev. Microbiol., 7: 287-296; U.S. Pat. No. 6,210,891; U.S. Pat. No. 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the SOLEXA®/ILLUMINA® platform (Voelkerding et al., Clinical Chem., 55: 641-658, 2009; MacLean et al., Nature Rev. Microbiol., 7: 287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, single-stranded fragmented DNA is end-repaired to generate $5^1$-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLID™ technology (Voelkerding et al., Clinical Chem., 55: 641-658, 2009; MacLean et al., Nature Rev. Microbiol., 7: 287-296; U.S. Pat. No. 5,912,148; U.S. Pat. No. 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLID™ system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the technology finds use in HELISCOPE® by Helicos BioSciences (Voelkerding et al., Clinical Chem., 55: 641-658, 2009; MacLean et al., Nature Rev. Microbiol., 7: 287-296; U.S. Pat. No. 7,169,560; U.S. Pat. No. 7,282,337; U.S. Pat. No. 7,482,120; U.S. Pat. No. 7,501,245; U.S. Pat. No. 6,818,395; U.S. Pat. No. 6,911,345; U.S. Pat. No. 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The ION TORRENT™ technology is a method of DNA sequencing based on the detection of hydrogen ions that are released during the polymerization of DNA (see, e.g., *Science* 327(5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the ION TORRENT™ sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

The technology finds use in another nucleic acid sequencing approach developed by Stratos Genomics, Inc. and involves the use of XPANDOMER™ reporter technology. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an XPANDOMER™ reporter of a length longer than the plurality of the subunits of the daughter strand. The XPANDOMER™ reporter typically includes the tethers and reporter elements for parsing genetic information in a sequence corresponding to the contiguous nucleotide sequence of all or a portion of the target nucleic acid. Reporter elements of the XPANDOMER™ reporter are then detected. Additional details relating to XPANDOMER™ reporter technology-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-58, 2009; U.S. Pat. No. 7,329,492; U.S. patent application Ser. No. 11/671,956; U.S. patent application Ser. No. 11/781, 166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

B. Detection Methods

In some embodiments, a computer-based analysis program is used to translate the raw data generated by the detection assay (e.g., the presence, absence, or amount of a given nucleic acid) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., presence or absence of a nucleic acid) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

In some embodiments, nucleic acids ligated using the methods described herein find use in a variety of research, screening and clinical applications, including but not limited to, in the fields of genomics, pharmacogenomics, drug discovery, food characterization, genotyping, diagnostics, gene expression monitoring, genetic diversity profiling, whole genome sequencing and polymorphism discovery, or any other applications involving the cloning or other ligation of nucleic acids.

A yet further aspect of the invention provides kit and systems comprising components necessary, sufficient or useful for performing ligation reaction. (e.g., adaptors, template for nucleic acid analysis reactions, enzymes, reagents, controls, etc.).

EXAMPLES

The following examples are provided to demonstrate and further illustrate certain embodiments of the present invention and are not to be construed as limiting the scope thereof.

Example 1

Random Fragmentation

A nucleic acid sample is randomly fragmented using a nucleic acid shearing device and the fragmented nucleic acids are mixed with enzymes and reagents capable of removing 3' nucleic acid overhangs, polymerizing nucleic acids opposite a 5' nucleic acid overhang, removing phosphates from 3' ends of nucleic acids, attaching phosphates to the 5' ends of nucleic acids, and producing a 3' nucleic acid overhang. A specific example of this is:

1) The use of polynucleotide kinase (PNK) and adenosine tri-phosphate (ATP) to remove 3' phosphates and attach 5' phosphates, 2) The use of T4 polymerase and dNTPs (dATP, dTTP, dCTP, dGTP, etc.) to remove 3' nucleic acid overhangs and polymerize nucleic acid strands opposite 5' nucleic acid overhangs, 3) The use of klenow polymerase without 3' or 5' exonuclease activity (klenow exo) and dNTPs to add a 3' nucleic acid overhang to the nucleic acid fragments.

These reactions performed in series produce nucleic acid fragments with 3' nucleic acid overhangs including multiple overhang sequences such as A, G, T, C, AA, AG, AT, AC, etc. These nucleic acid fragments are then mixed with a mixture of double stranded nucleic acid adaptors with distinct single stranded overhangs and T4 ligase to attach the adapter sequence (s) to the nucleic acid fragments. The nucleic acid library is then further processed using application specific purification and enzymatic treatments to prepare the library for sequencing or other use.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A kit, comprising:
a plurality of double stranded nucleic acid adaptors, wherein each of said plurality of adaptors has a distinct single stranded overhang relative to each other adaptor, wherein said adaptor overhangs have random nucleotide sequences complementary to a plurality of single stranded nucleotide overhangs of one or more double stranded nucleic acid inserts; and a ligase.

2. The kit of claim 1, wherein said plurality of double stranded nucleic acid adaptors comprises adaptor overhangs of 1 or 2 nucleotides.

3. The kit of claim 1, wherein said adaptor overhangs have single nucleotide overhangs at the 3' or 5' ends.

4. The kit of claim 3, wherein said adaptor overhangs are different and are selected from the group consisting of a, t, c, and g.

5. The kit of claim 1, wherein said plurality of double stranded nucleic acid adaptors comprises an adaptor overhang comprising c or g.

6. The kit of claim 1, wherein said adaptor overhangs have double nucleotide overhangs at the 3' or 5' ends.

7. The kit of claim 1, wherein two or more adaptors comprise adaptor overhangs that are different and are selected from the group consisting of aa, ag, at, ac, ga, gg, gc, gt, tt, tc, ta, tg, cc, ct, ca, and cg.

8. The kit of claim 1, wherein said plurality of adaptors comprises 2 or more, 3 or more, 4 or more, 5 or more, 6 or more, 7 or more, 8 or more, 9 or more, 10 or more, 11 or more, 12 or more, 13 or more, 14 or more, 15 or more or 16 or more distinct overhangs.

9. The kit of claim 1, wherein said plurality of double stranded nucleic acid adaptors comprises:
a) a first double stranded nucleic acid adaptor comprising an adaptor overhang of 1 or 2 nucleotides;
b) a second double stranded nucleic acid adaptor comprising an adaptor overhang of 1 or 2 nucleotides; and
c) a third double stranded nucleic acid adaptor comprising an adaptor overhang of 1 or 2 nucleotides,
wherein:
i) said adaptor overhang of said first double stranded nucleic acid adaptor is different than said adaptor overhang of said second double stranded nucleic acid adaptor; and
ii) each of said adaptor overhangs of said first and second double stranded nucleic acid adaptors is different than said adaptor overhang of said third double stranded nucleic acid adaptor.

10. The kit of claim 1, wherein two or more double stranded nucleic acid inserts comprise distinct nucleic acid sequences.

11. The kit of claim 1, wherein said single stranded nucleotide overhangs of said one or more double stranded nucleic acid inserts comprise a plurality of distinct sequences.

12. The kit of claim 1, wherein said single stranded nucleotide overhangs of said one or more double stranded nucleic acid inserts comprise overhangs of 1 or 2 nucleotides.

13. The kit of claim 1, further comprising at least one reagent for analyzing said one or more double stranded nucleic acid inserts.

14. The kit of claim 13, wherein said reagent is a reagent for nucleic acid sequencing selected from the group consisting of pyrosequencing, sequencing-by-ligation, sequence-by-synthesis (SBS), nanopore sequencing, and oligonucleotide extension sequencing.

15. The kit of claim 1, wherein each adaptor of said plurality of double stranded nucleic acid adaptors comprises a detection label.

* * * * *